(12) United States Patent
Larson et al.

(10) Patent No.: US 11,957,548 B2
(45) Date of Patent: Apr. 16, 2024

(54) MOLDABLE SPLINT AND METHOD OF USING SAME

(71) Applicants: Peter M. Larson, Garnville, OH (US); Mary Ellen Devault, Newark, OH (US)

(72) Inventors: Peter M. Larson, Garnville, OH (US); Mary Ellen Devault, Newark, OH (US)

( * ) Notice: Subject to any disclaimer, the term of this patent is extended or adjusted under 35 U.S.C. 154(b) by 247 days.

(21) Appl. No.: 17/577,963

(22) Filed: Jan. 18, 2022

(65) Prior Publication Data
US 2023/0225907 A1  Jul. 20, 2023

(51) Int. Cl.
| A61F 5/00 | (2006.01) |
| A61F 5/058 | (2006.01) |
| A61F 13/04 | (2006.01) |
| A61L 15/14 | (2006.01) |

(52) U.S. Cl.
CPC .......... *A61F 13/04* (2013.01); *A61F 5/05825* (2013.01); *A61L 15/14* (2013.01)

(58) Field of Classification Search
None
See application file for complete search history.

(56) References Cited

U.S. PATENT DOCUMENTS

| 6,991,610 | B2 * | 1/2006 | Matsumoto | A61F 5/01 602/8 |
| 7,329,229 | B2 * | 2/2008 | Scheinberg | A61F 5/0111 602/5 |
| 2015/0065932 | A1 * | 3/2015 | Larson | A61F 5/058 602/12 |
| 2016/0067078 | A1 * | 3/2016 | Larson | A61F 5/41 602/7 |
| 2017/0189241 | A1 * | 7/2017 | Joseph | A61F 5/0111 |

* cited by examiner

*Primary Examiner* — Kim M Lewis
(74) *Attorney, Agent, or Firm* — Michael J. Gallagher; Luper Neidenthal & Logan

(57) ABSTRACT

A composite moldable splint and method for using the same is described. In some embodiments, the splint has at least a partially fluid-filled inner volume, which in some embodiments may include foam, rubber, water, or pelletized material, enclosed by a flexible liner, surrounded by a thermoplastic layer that is flexible and moldable when heated. The inner volume, which may include a thermoactive adhesive having differing viscosity characteristics at a plurality of temperatures, provides the ability to mold the cushion into a wide range of shapes and contours, such as when forming around a body part. The thermoplastic layer provides the ability of the cushion to be molded when heated, while the inner volume tends to maintain a shape, and allows the thermoplastic layer to stay in its formed shape as the cushion cools. The cushion may be used in a range of medical applications for stabilizing patients and body parts.

21 Claims, 14 Drawing Sheets

MOLDABLE SPLINT AND METHOD OF USING SAME

CROSS-REFERENCE TO RELATED APPLICATIONS

This application is a continuation-in-part of U.S. patent application Ser. No. 14/938,983, filed Nov. 12, 2015; all of which is incorporated by reference as if completely written herein.

STATEMENT REGARDING FEDERALLY SPONSORED RESEARCH OR DEVELOPMENT

Not applicable.

TECHNICAL FIELD

The present disclosure relates generally to a low density moldable splint, in particular, for making an anatomically high-accuracy moldable splint well-suited for patient immobilization during radiotherapy or other applications requiring a high degree of accuracy in patient positioning.

BACKGROUND OF THE INVENTION

The present invention relates to a position-retaining device, which may be interchangeably described as a pillow, splint, cast, or other terms as would be known in the art, for persons whose bodies or body parts are required to be retained in a particular position or attitude. For the purposes of this specification, the device will be most commonly referenced as a "splint." More particularly, it relates to a position-retaining splint which can be made to conform to the configuration of a person's body or body part to provide an anatomically high-accuracy position-retaining device. The splint can be used, among other purposes, to retain the person's body or body part in a required position or attitude with the pressure from the body or body part being distributed uniformly and effectively on the position-retaining device. The device, in certain embodiments, is particularly well-suited for patient positioning during radiotherapy or other procedures, due to its relatively low density and high radiolucency, in which high accuracy and consistent repeatability in positioning are important. The present invention also relates to a method of using the position-retaining device.

The use of low-temperature thermoplastics for patient positioning is well-known and dates back to splinting devices invented in the 1960's (Larson, U.S. Pat. No. 5,540,876). Splints are heated, usually in hot water, to a temperature of about 160° F., whereupon they become pliable and can be molded by hand directly on the patient's body part. These devices are well known in the field of occupational therapy and include splints with padding or cushioning material laminated to the thermoplastic to provide comfort against the patient's skin.

Plastic materials have been successfully used in the past for making splints, casts and the like. U.S. Pat. No. 3,490,444 describes the use of thermoplastic polydienes like transpolyisoprene and transpolychloroprene, which melt between 140° F. (60° Celsius) and 212° F. (100° Celsius), and which harden by crystallization at about 140° F. (60° Celsius), such that these plastics can be formed for use as a body supporting member. Poly (epsilon-caprolactone) (PCL) has also been found to be an excellent splint or cast material (U.S. Pat. No. 4,144,223). Polyurethanes based on prepolymers of poly (epsilon-caprolactone) have also been used (U.S. Pat. No. 4,316,457).

As described in earlier patents, the polymers can be heated in hot water at a temperature usually exceeding 122° F. (50° Celsius) and up to about 212° F. (100° Celsius), whereby they become soft, self-adherent and sufficiently pliable to be deformed and shaped as a cast, splint or protective device. When allowed to cool in air to about 140° F. (40° Celsius), the materials will remain pliable, moldable and cohesive for a period of several minutes, exhibiting a hysteresis, as described in U.S. Pat. No. 3,490,444. During this time the splint, cast or device can be molded directly to the patient without discomfort, and the shaped plastic sets hard by crystallization to assume a rigid form as a useful body support member or protective device.

Splints and casts made of the aforementioned materials provide good support strength, due to the hardness of the cooled materials. PCL, for example cools to a hardness of between 45 and 55 (Shore D), very suitable for a splint or cast, but too hard and uncomfortable for a pillow or a neck brace, for example. Cushioning fabrics are often used with splints to mitigate the hardness of the thermoplastic against the skin.

The aforementioned thermoplastics by themselves are also ill-suited for moldable pillows and formable underlying body supports because of the impracticality of heating and forming times found with suitably thick materials, as can be seen in the Example below. A 3.2 mm splinting sheet of PCL can typically be heated to forming in about a minute in hot water at 160° F. A device of 3 cm thickness or more would take 15 minutes or more to heat, and then a half hour or more to cool to hardness.

Example 1

Rectangular (10"×10") sheets of 100% polycaprolactone were heated in hot water at 160° F. (71° C.). Times to achievement of sufficient flexibility for molding were assessed as follows:

| Thickness of 100% Polycaprolactone Sheet (millimeters) | Time (seconds) to Flexibility |
|---|---|
| 1.6 mm | 22 sec. |
| 2.4 mm | 48 sec. |
| 3.2 mm | 72 sec. |
| 8.4 mm | 275 sec. |
| 104 mm | 1,110 sec. (18.5 minutes) |

Unsurprisingly, as can be seen from the above data, heating times do not increase in a linear fashion, e.g., a doubling of the thickness from 1.6 mm to 3.2 mm results in more than a tripling of the heating time.

In the field of radiation therapy, precise patient positioning is essential for treatment accuracy. An additional requirement is that patients be precisely re-positioned for repeated radiation treatments. This requires the positioning to be reproduced accurately each time the patient undergoes a treatment. Another requirement is for relatively low density, i.e., high radiolucency. Low-temperature thermoplastic masks are often used for such positioning. Masks are heated to a temperature of about 160° F. (71° C.), and formed directly on to the patient's head or other body part. The masks may be affixed to a table supporting the patient and cooled to form a firm mask holding the patient steady for treatment. After treatment, the mask may be removed. When the patient returns for the next treatment, the mask is releasably reattached, holding the patient in a reproduced position for treatment.

Various masks are used for radiation therapy treatments, including stereotactic head masks holding the top and bottom of the patient's head (Vilsmeier, U.S. Pat. No. 5,702, 406). Another method of stabilizing the patient's head position includes the use of a moldable cushion or pillow. Hirano (U.S. Pat. No. 6,254,959) teaches a method of making a position-retaining device utilizing a mixture of elastic granules and water-curable resin. The resin and granule mixture is encased in a fabric to make a pillow, cushion or patient support device that can be shaped to a head or other body part and then hardened by adding water to the resin. The cushion is stored in a sealed package before use to prevent premature hardening due to atmospheric or other environmental moisture. When removed from the package and exposed to water the cushion begins to harden. It is placed under the patient's head or other body part to conform to the patient and also to the underlying support structure. The cushion then hardens to become a secure conforming positioning device, suitable for reproducible treatment positioning.

The water-activated resin devices are also known to have spheroidal bodies inside them such as relatively small plastic beads having a diameter of from 1 to 5 mm, which are mixed in with the resin to form a slurry-like material. The slurry is surrounded by a fabric barrier to prevent patient contact with the slurry and to provide patient comfort. Water is applied to the fabric and seeps in to the slurry to activate the hardening of the resin. A significant limitation of such devices is that once hardened, the devices cannot be modified or remolded. Additionally, the devices must be kept scrupulously dry until ready for use. Such water-active resin devices are also not suitable for changes in conformation during a course of time. If positioning needs to be adjusted, the device must be discarded and a new one made.

Another method of patient stabilization is the use of a vacuum apparatus, which is a hermetically sealed bag containing sphere-like bodies, such as relatively small plastic beads having a diameter of from 1 to 5 mm. The patient is placed on the bag, causing the beads to be displaced and conform around the patient. A vacuum pump may be then connected to the bag, and air is evacuated from the bag through a valve that can be closed to prevent air from re-entering the bag. This creates a vacuum state in the interior of the bag, which prevents the sphere-like bodies from moving, thereby holding the bag and the patient in a fixed position. This positioning device is suitable for repeat treatments once the vacuum is applied, positon cannot be easily altered. This vacuum apparatus is also known to be used to position patients for other medical procedures, such as in operating rooms. A limitation of the device is that the bags can be easily punctured by a scalpel, syringe or knife. Should any air leak into the device, it loses its conformation and positioning must begin anew. The device also has no elasticity or air-permeability and is not comfortable for extended treatment times.

SUMMARY OF THE INVENTION

The disclosed invention relates to methods to for making a moldable splint. The splint includes a hollow fluid-filled thermoplastic shell that may be heated to conform to a body part and then cooled to retain its molded shape. The hollow volume of the shell may be filled with a wide variety of fluids, and in one particular embodiment is filled with a mixture of pellets and thermoactive binder. In certain embodiments, these pellets are hollow spheres, which give decreased density, i.e., increased radiolucency, to the finished splint. In some embodiments a thermoactive binder having a biphasic response curve is utilized. Such a biphasic response may involve having a binder that is relatively thin (low-density) consistency at the temperature range in which the mixture of pellets and binder is formed, while having a relatively thicker (higher-density) consistency at the working temperature for forming a splint. The consistency of the pellets and binder is such that at the working temperature it will hold the thermoplastic shell in its formed position, obviating the need for an outside molding form. The shell may have an outside covering made from a wide variety of materials, some of which are discussed in more detail. Illustrative examples of various embodiments of the invention, all provided by way of example and not limitation, are described. Some embodiments may have an internal liner separating the shell from the hollow volume, the advantages of which are discussed below.

BRIEF DESCRIPTION OF THE ILLUSTRATIONS

Without limiting the scope of the as disclosed herein and referring now to the drawings and figures.

Figure 1:
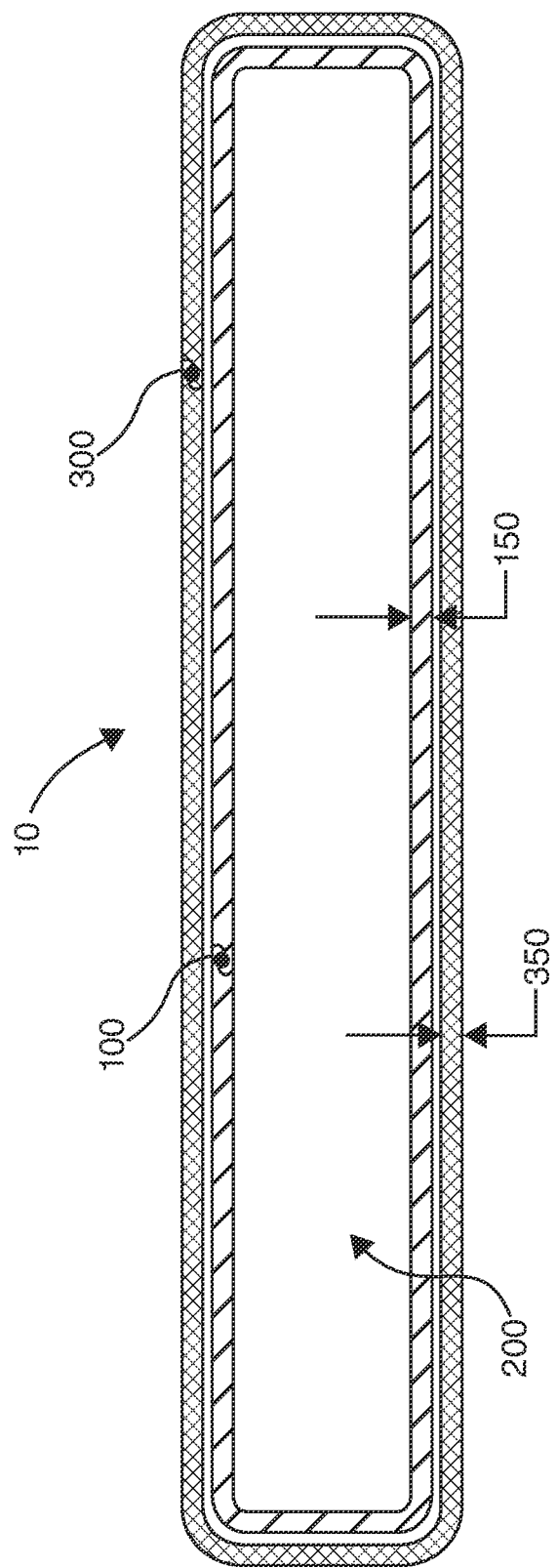
FIG. 1 is a cross-sectional view of an embodiment of a moldable splint.

These illustrations are provided to assist in the understanding of the exemplary embodiments of the method of forming a moldable splint and materials related thereto described in more detail below and should not be construed as unduly limiting the specification. In particular, the relative spacing, positioning, sizing and dimensions of the various elements illustrated in the drawings may not be drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

Figure 4:
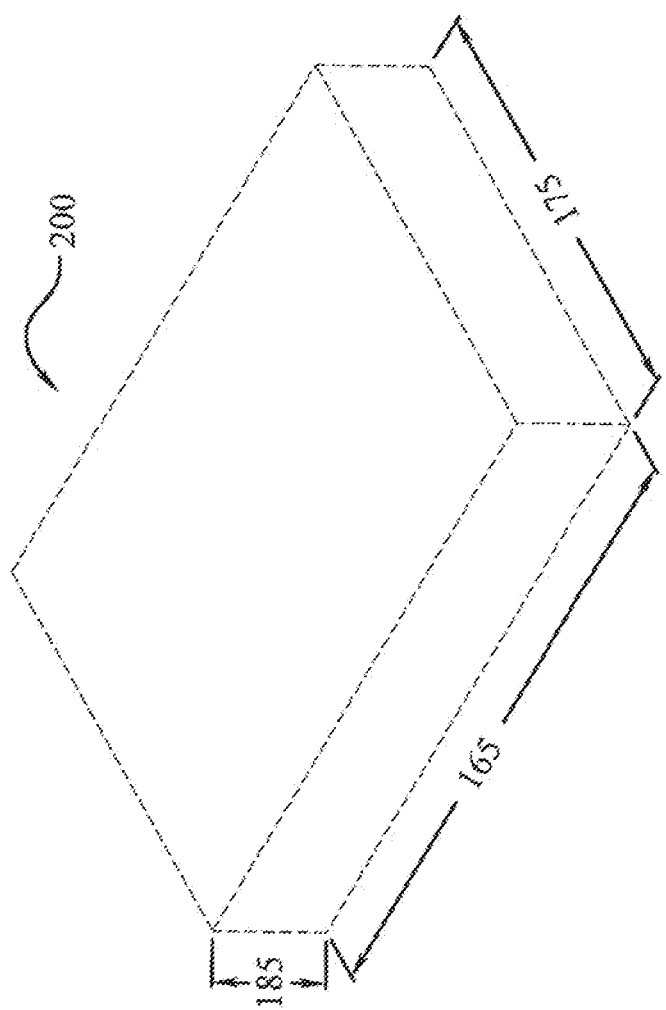
FIG. 4 is an elevated perspective view of the inside aspect of a hollow thermoplastic shell of an embodiment of a moldable splint, showing shell interior dimensions.

As used in this specification, the terms "about," "approximately," or similar language is intended to express a range of generally +/−15% from the value stated. What is claimed then, as seen in FIGS. 1-9, is a moldable splint (10) with a thermoplastic shell (100), as seen well in FIGS. 1 and 3, having a shell material thickness (150), and a three-dimensional structure having a first shell outside linear dimension (160), a second shell outside linear dimension (170) and a third shell outside linear dimension (180). In typical embodiments, such as one seen well in FIG. 3, the first shell outside linear dimension (160) may be thought of as the "length" of the splint, the second shell outside linear dimension (170) may be thought of as the "width" of the splint, and the third shell outside linear dimension (180) may be thought of as the "thickness" of the splint, but there is no reason that such labeling be fixed. Such dimensions are not intended to specify only a rectangular embodiment, and round, triangular or other geometric shapes are expressly contemplated as alternate embodiments, as are free-form or irregular shapes that may be dictated by certain applications. The shell is hollow and closed from the outside environment, and encloses a partially or fully fluid-filled volume (200), seen well in FIG. 4, that is bounded by a first shell inside linear dimension (165), a second shell inside linear dimension (175), and a third shell inside linear dimension (185), each representing an inside surface of the shell (100). Embodiments are not limited to those where the "fluid" is a liquid, as alternate embodiments where the fluid is a gas, or a combination of gas and liquid are expressly envisioned. As seen in one embodiment in FIG. 3, the first shell outside linear dimension (160) is equal to or greater than the second shell outside linear dimension (170), and the third shell outside linear dimension (180) is less than or equal to the second shell outside linear dimension (170). Correspondingly, as seen in FIG. 4, the first shell inside linear dimension (165) is greater than or equal to the second shell inside linear dimension (175), and the third shell inside linear dimension (185) is less than or equal to the second shell inside linear dimension (175).

Figure 6:
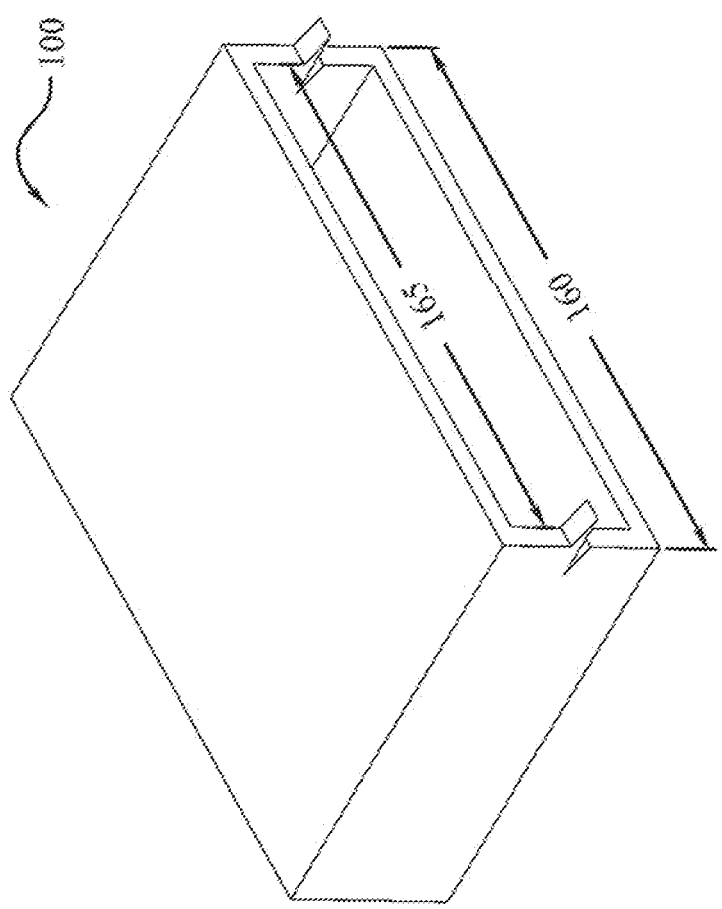
FIG. 6 is an elevated perspective cross section view in a first linear direction of the embodiment of FIGS. 3 and 4.
Figure 7:
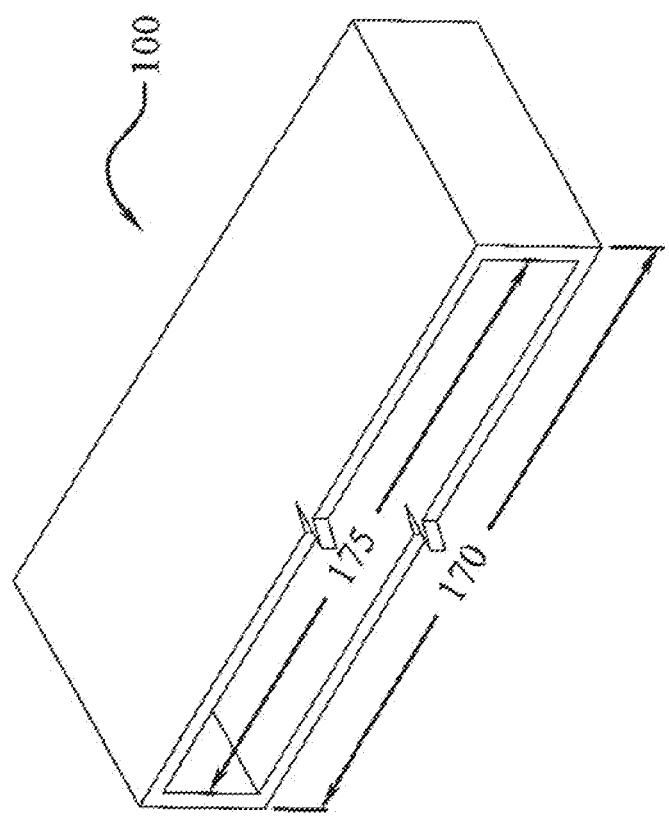
FIG. 7 is an elevated perspective cross section view in a second linear direction of the embodiment of FIGS. 3 and 4.
Figure 8:
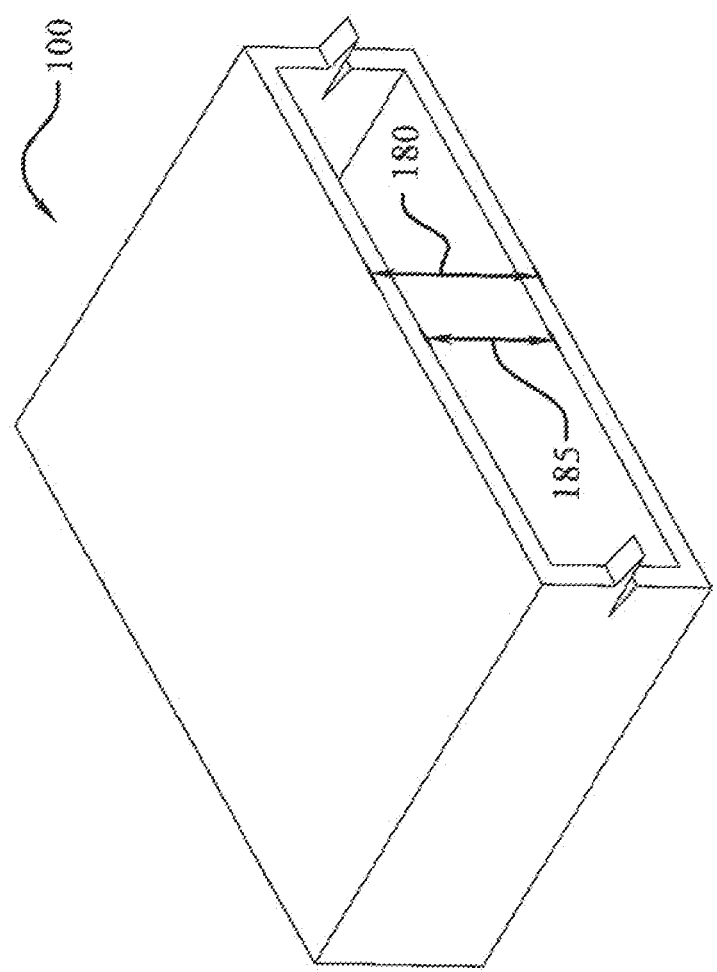
FIG. 8 is an elevated perspective cross section view in a third linear direction of the embodiment of FIGS. 3 and 4.

The shell (100) is envisioned in at least in some embodiments, such as one seen in FIG. 4, to be wider and longer than it is thick, and have a minimum overall thickness (which in many embodiments may comprise the third shell outside diameter 180) being greater than the shell material thickness (150), such that the third shell outside linear dimension (180), the first shell inside linear dimension (165), the second shell inside linear dimension (175), and the third shell inside linear dimension (185) are all equal to or greater than the shell material thickness (150), as seen well in FIGS. 6, 7 and 8.

Figure 5:
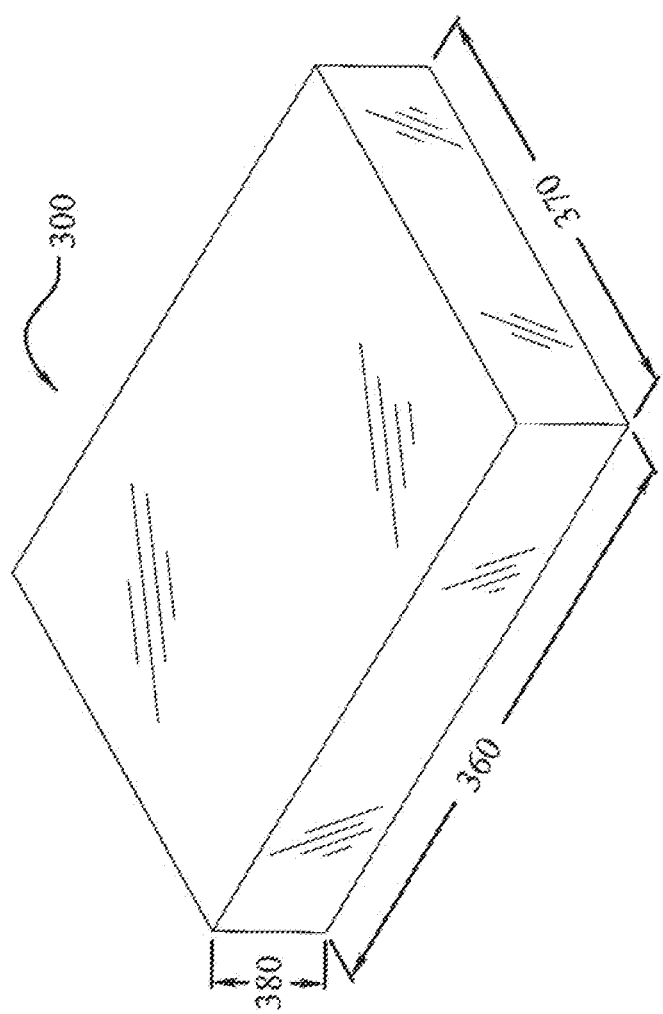
FIG. 5 is an elevated perspective view of an outside cover of the embodiment of FIGS. 3 and 4.

In some embodiments, shown well in FIGS. 1 and 5, the thermoplastic shell (100) may, substantially for comfort for the user, be enclosed by a flexible outer covering (300) having an outer covering thickness (350), at least a first covering length (360), at least a first covering width (370) and at least a first covering height (380). In some embodiments, the flexible outer covering (300) may be no more than a thin coating adhered to or otherwise applied to the surface of the shell (100). In other embodiments, the flexible outer covering (300) may be more substantial, and may include a fabric material. The flexible outer covering (300) may be a fabric outer layer (300), and it may simply surround all or part of the shell (100), or it may be bonded to the thermoplastic shell (100).

Figure 2:
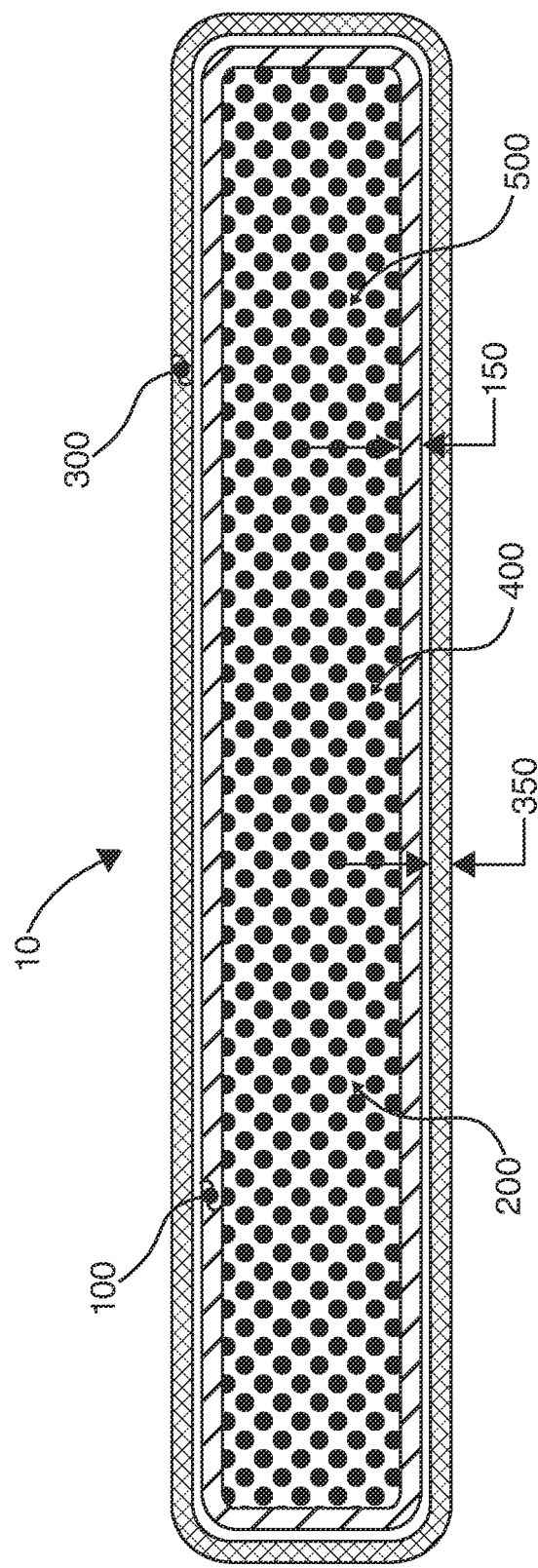
FIG. 2 is a cross-sectional view of another embodiment of a moldable splint.
Figure 3:
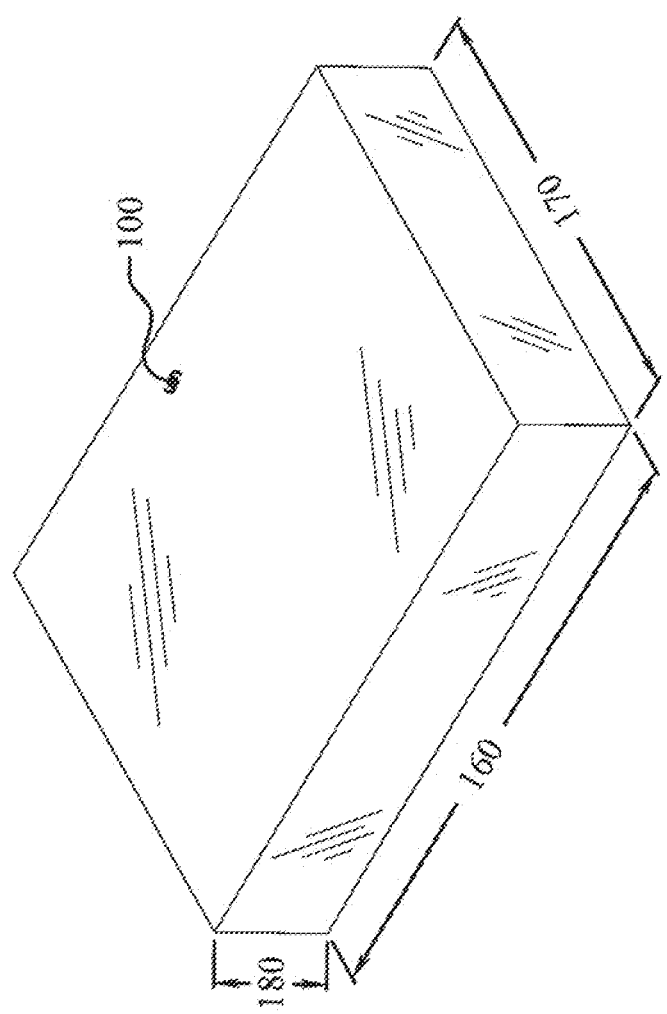
FIG. 3 is an elevated perspective of the outside aspect of a hollow thermoplastic shell of an embodiment of a moldable splint, showing shell exterior dimensions.

In other embodiments, such as seen in FIGS. 1 and 2, the flexible outer covering (300) may display considerable elasticity, enabling it to stretch tightly around the shell (100), and in one particular embodiment, by way of example only and not limitation, the flexible outer covering (300) may be stretchable in at least two dimensions to at least a second covering length (not shown) that is equal to or greater than 150% of the at least a first covering length (360) and to at least a second covering width (not shown) that is equal or great than 150% of the at least a first covering width (370).

Various dimensions and materials are appropriate for the flexible outer covering (300) which may have an outer covering thickness (350) of between about 1 millimeter and about 5 millimeters, and may be made, by way of example only and not limitation, out of nylon, cotton, neoprene, and blends thereof.

The shell (100) may be made from a wide variety of materials. In some embodiments the thermoplastic shell (100) may include a thermoplastic having a melting temperature between about 140° F. (60° Celsius) and 212° F. (100° Celsius) and a crystallization temperature of about 140° F. (60° Celsius). In certain embodiments, as would be known by one skilled in the art, the thermoplastic shell (100) material may be selected, again by way of example only and not limitation, from the group of thermoplastics consisting of poly (epsilon-caprolactone) (PCL), transpolyisoprene, transpolychloroprene and mixtures thereof. In one particular set of embodiments, the thermoplastic shell (100) may have a shell material thickness (150) of between about 1 millimeter and 4 millimeters.

As noted, the shell (100) may enclose a volume (200), seen in FIG. 4, that is filled with a wide variety of fluids, in particular, not limited to liquids or semi-liquids. In one embodiment the partially fluid filled volume (200) may include, in addition to fluid, a number of pellets (400) having at least one partially rounded edge, as seen in FIG. 2.

Again as seen in FIG. 2, in some embodiments, the pellets (400) may generally have a first substantially spheroidal body shape, wherein many or most of the pellets will have a diameter of approximately 1 millimeter to 6 millimeters at a temperature of about 70° F. (21° C.). In some embodiments, the pellets (400) may have a nominal density of about 1 lb. per cubic foot, and/or a compressive strength (at 10% deformation) of approximately 10.0 pounds per square inch, and/or a minimum flexural strength of approximately 25.0 pounds per square inch.

In certain embodiments, many or most of the pellets (400) will retain a second substantially spheroidal shape within 10% of the first substantially spheroidal shape when exposed to temperatures greater than 100° F. (38° C.) and less than 250° F. (93° C.).

In some embodiments, many or most of the pellets (400) will have a hollow spheroidal shape. In addition to other advantages, a hollow spheroidal shape decreases the density of the pellets, and therefore of the final product, enabling increased radiolucency of a finished splint.

The pellets (400) may be formed from a wide variety of materials, including, by way of example only and not limitation; polystyrene, ABS plastic, nylon, neoprene, polyethylene, polypropylene and mixtures thereof.

In yet another series of preferred embodiments, seen in FIG. 2, a thermoactive binder (500) may be mixed with the pellets (400) and may include such materials as resins, waxes, glues or mixtures including these materials.

In one series of embodiments, the splint includes an inner slurry of thermoactive binder and hollow spheroidal pellets. The inner slurry may contain hollow polystyrene pellets coated with a mild adhesive of a type known to those skilled in the art as a "fugitive adhesive" due to its easy release from most substrates. In some embodiments "3M Hot Melt Adhesive 3798 LM" (3M CORPORATION®, Minneapolis, MN U.S.A.) has been shown useful. The use of such a "fugitive adhesive" allows the coated pellets to hold a position, but can be easily manipulated and shaped to any new position by nature of the easy release characteristics of the adhesive, and has been shown helpful in creating moldability characteristics of the slurry.

Figure 9:
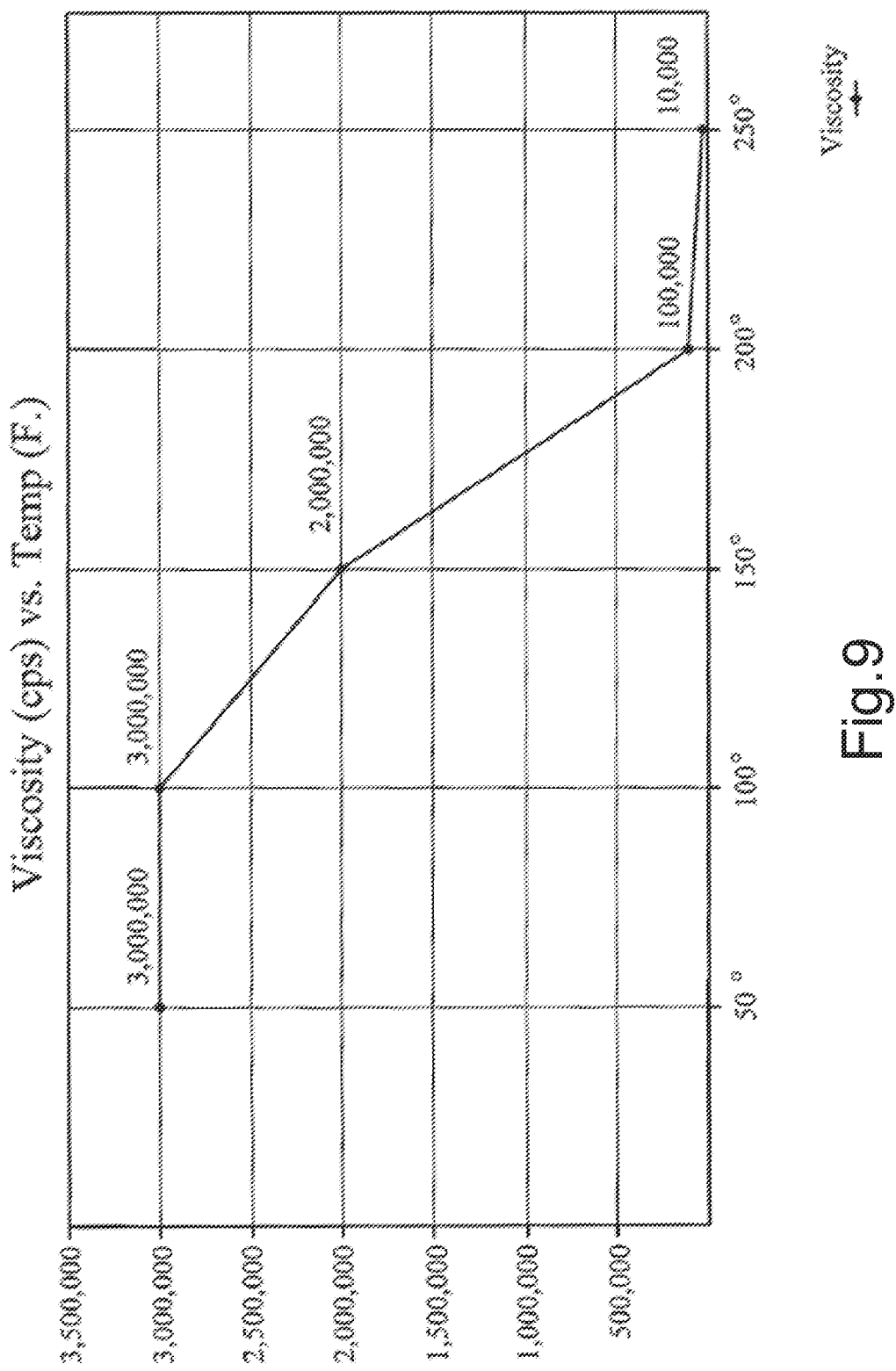
FIG. 9 is a graph of viscosity according to temperature of an embodiment of a thermoactive binder as employed in some embodiments of the invention, showing the relative decrease in viscosity (centipoise, or cps) with increases in temperature (degrees Fahrenheit).

Such an adhesive tends to have a biphasic viscosity response to temperature, as seen well in FIG. 9. At temperatures wherein the slurry may be compounded, i.e. at about 250° F., the adhesive becomes relatively thin, having a viscosity of approximately 9,500 cps at 250° F. and displaying a relatively flat response of viscosity to changes of temperature in this temperature range. This allows the pellets to be quickly and gently mixed to fully coat them with the adhesive. The viscosity of the adhesive may be from 5000 to 10,000 cps at 250° F. in order to be successfully mixed with the polystyrene pellets. Pellets and adhesive are quickly and gently mixed to coat all the pellets with the adhesive. Higher viscosity requires rougher mixing which may deform and deflate the pellets. Lower viscosity will not adequately adhere to and coat the pellets. In the working temperature range of the splint, the adhesive also displays a relatively flat response of viscosity to changes of temperature, i.e., within the temperature range of ~50°-150+° F.

The pellets optimally maintain their hollowness and consistent shape, in order to achieve the low density required for successful use as a patient support device for radiation therapy. Low density means increased radiolucency and minimal attenuation of the radiation beams to the patient. Higher mixing temperatures may also damage the pellets during the mixing process. At higher temperatures the pellets themselves will melt and deform, resulting in an adhesive-pellet slurry that has a higher density, unacceptable for radiotherapy functions.

The thermoactive binder (500) may have varying performance parameters. In various series of embodiments, the thermoactive binder (500) may have a dynamic viscosity of between approximately 100 and 500 pascal-seconds. (Pa·s). In some embodiments the thermoactive binder (500) may have a dynamic viscosity of approximately 300 pascal-seconds (Pa·s). In other embodiments, the thermoactive binder (500) may have a penetration flow of approximately of approximately 86-110 dmm at about 75° F. (25° C.).

In one particular embodiment, the splint may be formed to have a thermoplastic shell (100) having a shell material thickness (150), a first shell outside linear dimension (160), a second shell outside linear dimension (170) and a third shell outside linear dimension (180) This shell (100) may enclose an at least partially fluid-filled volume (200) comprising a plurality of pellets (400) having at least one partially rounded edge and a thermoactive binder (500). The plurality of pellets (400) may be mixed with the thermoactive binder (500) in a ratio by weight of approximately 2:1 The volume may be closed to an external atmosphere and bounded by a first shell inside linear dimension (165), a second shell inside linear dimension (175), and a third shell inside linear dimension (185).

The first shell outside linear dimension (160) may be equal to or greater than the second shell outside linear dimension (170), and the third shell outside linear dimension (180) may be less than or equal to the second shell outside linear dimension (170). The first shell inside linear dimension (165) may be greater than or equal to the second shell inside linear dimension (175), and the third shell inside linear dimension (185) may be less than or equal to the second shell inside linear dimension (175).

As to relationships between the various dimensions of the shell (100), the first shell outside linear dimension (160), the second shell outside linear dimension (170), the third shell outside linear dimension (180), the first shell inside linear dimension (165), the second shell inside linear dimension (175), and the third shell inside linear dimension (185) may all be equal to or greater than the shell material thickness (150).

In yet another particular embodiment, the splint (100) may be formed to have a thermoplastic shell (100) having a shell material thickness (150), a first shell outside linear dimension (160), a second shell outside linear dimension (170) and a third shell outside linear dimension (180). The shell (100) may further enclose an at least partially fluid-filled volume (200) comprising a plurality of pellets (400) having at least one partially rounded edge and a thermoactive binder (500) mixed with the plurality of pellets (400). The volume (200) may be closed to an external atmosphere and bounded by a first shell inside linear dimension (165), a second shell inside linear dimension (175), and a third shell inside linear dimension (185). In this embodiment, the first shell outside linear dimension (160) may be equal to or greater than the second shell outside linear dimension (170), and the third shell outside linear dimension (180) may be less than or equal to the second shell outside linear dimension (170). The first shell inside linear dimension (165) may be greater than or equal to the second shell inside linear dimension (175), and the third shell inside linear dimension (185) may be less than or equal to the second shell inside linear dimension (175).

As to relationships between the various dimensions of the shell (100), the first shell outside linear dimension (160), the second shell outside linear dimension (170), the third shell outside linear dimension (180), the first shell inside linear dimension (165), the second shell inside linear dimension (175), and the third shell inside linear dimension (185) may all be equal to or greater than the shell material thickness (150).

In this embodiment, the thermoplastic shell (100) may be enclosed by a flexible outer covering (300) having an outer covering thickness (350), at least a first covering length (360), at least a first covering width (370), and at least a first covering height (380). The flexible outer covering (300) may be stretchable in at least two dimensions to at least a second covering length (365) that is equal to or greater than 150% of the first covering length (360) and to at least a second covering width (375) that is equal or great than 150% of the first covering width (370) (not illustrated).

The shell has performance characteristics associated with temperature as well. Because shells have a surrounding layer of polycaprolactone, the clinical molding temperature of the cushions will be from 150° to 175° F. This is standard temperature range in radiation therapy clinics for masks, and is the optimal temperature for forming the polycaprolactone. So it is essential (for practical use and also due to the polycaprolactone) for the cushions to be easily moldable in this temperature range. So, too, the adhesive in the slurry must exhibit its "easy release" in this temperature range.

FIG. 9 documents a typical viscosity curve. One skilled in the art will realize as a practical matter that in the range of clinical forming (150° to 175° F.) the outer shell will be relatively flexible and moldable, while the inner slurry will be somewhat stiff, yet moldable, and tend to hold a position. This allows the inner adhesive-pellet slurry to tend to hold a shape while the outer shell is cooling and hardening. Once the outer shell hardens, it tends to provide support for the viscous, but still moldable, inner adhesive-pellet slurry.

One skilled in the art will appreciate, for general guidance sake, that the following commonly found substances correspond to various approximate viscosities at 70° F., as shown:

TABLE 1

Relative Viscosities of Some Commonly Found Compounds

| Substance | Viscosity (centipoise/cps) |
|---|---|
| Water | 1-5 |
| Ethylene Glycol (Antifreeze) | 15 |
| SAE 30 Motor Oil or Maple Syrup | 150-200 |
| SAE 60 Motor Oil or Glycerin | 1,000-2,000 |
| Blackstrap Molasses | 5,000-10,000 |
| Ketchup or Mustard | 50,000-70,000 |
| Shortening or Lard | 1,000,000-2,000,000 |
| Window Putty | ~100,000,000 |

While there are various methods to activate and form various embodiments of the moldable splint of the current application, two preferred embodiments, intended by way of example only, and not limitation, include water bath or oven heating methods.

In one embodiment of water-bath forming, again intended by way of example only and not limitation, a water bath may be prepared having a water temperature of between approximately 160° to 180° F. (71° to 82° Celsius). Such temperatures will be expected to result in a time to suitable softening in the bath of approximately four to five minutes. In order to prevent the outer layer from becoming wet, the moldable splint may be left in a water impermeable outer cover. After approximately five minutes, the moldable splint should be hand-checked for desired softness, but may be left in the water as long as necessary to achieve the desire softening. This time may extend to approximately, or even more than, ten minutes.

The moldable splint may then be removed from the water bath and molded to the target body part. By way of example only and not limitation, if the target body part were the head, the moldable splint could then be directly molded to any appropriate part of the head and/or neck. Equally well, the moldable splint could be placed on any firm surface on which molding is to take place, and a body part gently pressed against the splint. In the case where the moldable splint might be used for immobilizing a patient's head, the moldable splint may be placed on a suitable firm headrest, and then the patient's head may be placed on the splint. Gentle pressure on the head will then deform the splint between the headrest and head to fit the head precisely. As a result of the water bath heating, the splint will be warm and many users report it as being very comfortable, and even as having a calming effect on the patient.

The user, who may be a health care professional, holds the patient's target body part to be immobilized, which may the patient's head, on or slightly pressed into the splint until the splint begins to harden as a result of exposure to room air. The moldable splint will begin to firm after approximately 3 or 4 minutes in room air. The splint will generally reach full set-up firmness within 10 to 15 minutes. Minor adjustments to the position or fit can be made by locally reheating various areas with a heat gun, hair dryer, or other suitable heat source. Major adjustment may be more easily accomplished by placing the splint back in the water impermeable outer packaging, closing the packaging in a water resistant manner, and replacing the splint in the water bath for reheating. As the heating produces a three-way flexibility in the splint, the splint may be stretched to a longer length or width as desired, or may be compressed to a shorter length and width.

In one embodiment of an oven-heating method, again intended by way of example only and not limitation, a convection oven may be a preferred instrumentality, as the nature of convection ovens tends to produce an evenly distributed heating pattern.

In one embodiment, the oven temperature may be raised to approximately 165° F. (74° C.). Since in oven-heating embodiments, a dry heat is provided that does not wet the outer layer of the splint, the splint may be removed from the water impermeable packaging before heating.

In one embodiment, the room-temperature splint may be placed on a middle rack of the convection oven, while the oven is maintained, as mentioned, at a temperature of approximately 165° F. (74° C.). The splint will become moldable in about 10 to 15 minutes; however, longer heating times are unlikely to have any adverse effects.

After removal from the oven, the splint may be allowed to cool for 2 to 3 minutes to facilitate patient comfort. As with the water-bath heating embodiments, the splint may then be directly molded against any body part, or may be placed on any firm surface, and molding accomplished by pressing the body part against the splint. The user, who may be a health care professional, holds the patient's target body part to be immobilized, which may the patient's head, on or slightly pressed into the splint until the splint begins to harden as a result of exposure to room air. The splint will be warm and very comfortable, and as before, may often have a calming effect on the patient. The splint will begin to firm after approximately 3 or 4 minutes and will reach full set up hardness within 10-15 minutes. Minor adjustments to the position or fit can be made by locally reheating various areas with a heat gun, hair dryer, or other suitable heat source. Major adjustment may be more easily accomplished by placing the splint back in the oven or other heat source for reheating.

It is particularly to be emphasized that virtually any local or general heat source may be used to heat the splint to a conformational state, so long as that heat source is capable of reaching and maintaining the necessary temperatures. While heating methods that may involve wetting the outer layer are generally avoided for the sake of patient comfort, such wetting does not affect or compromise the integrity or utility of the splint.

In a further series of embodiments, seen well in FIGS. 1-9, a moldable splint (10) may include a thermoplastic shell (100) having a shell material thickness (150), a first shell outside linear dimension (160), a second shell outside linear dimension (170) and a third shell outside linear dimension (180). These dimensions may enclose an at least partially fluid-filled volume (200) closed to an external atmosphere and bounded by a first shell inside linear dimension (165), a second shell inside linear dimension (175), and a third shell inside linear dimension (185).

The first shell outside linear dimension (160) may be equal to or greater than the second shell outside linear dimension (170), and the third shell outside linear dimension (180) may be less than or equal to the second shell outside linear dimension (170). The first shell inside linear dimension (165) may be greater than or equal to the second shell inside linear dimension (175), and the third shell inside linear dimension (185) may be less than or equal to the second shell inside linear dimension (175).

The first shell outside linear dimension (160), the second shell outside linear dimension (170), the third shell outside linear dimension (180), the first shell inside linear dimension (165), the second shell inside linear dimension (175), and the third shell inside linear dimension (185) may all be equal to or greater than the shell material thickness (150).

In some embodiments, the thermoplastic shell (100) may be enclosed by a flexible outer covering (300) having an outer covering thickness (350), at least a first covering length (360), at least a first covering width (370), and at least a first covering height (380).

The thermoplastic shell (100) may be a thermoplastic having a melting temperature between about 140° F. (60° Celsius) and 212° F. (100° Celsius) and a crystallization temperature of about 140° F. (60° Celsius). The shell material thickness (150) may be between about 1.0 millimeters and 4.0 millimeters.

The thermoplastic shell (100) may include a thermoplastic selected from the group of thermoplastics consisting of poly (epsilon-caprolactone) (PCL), transpolyisoprene, transpolychloroprene and mixtures thereof, and may further include a cross-linked poly (epsilon-caprolactone) (PCL) having a shell material thickness (150) of between about 1.0 millimeters and 4.0 millimeters.

In another series of embodiments, the at least partially fluid filled volume (200) may include a plurality of pellets (400) having at least one partially rounded edge. In some embodiments, each of this plurality of pellets (400) may have a first substantially hollow substantially spheroidal body having a diameter of approximately 1 millimeter to 6 millimeters at a temperature of about 70° F. (21° C.). Such pellets may also have a nominal density of about 1 lb. per cubic foot and/or a compressive strength (at 10% deformation) of approximately 10.0 pounds per square inch, as well as a minimum flexural strength of approximately 25.0 pounds per square inch.

In certain embodiments, a plurality of the pellets (400) will retain a second substantially spheroidal shape within 10% of the first substantially spheroidal shape when exposed to temperatures greater than 100° F. (38° C.) and less than 250° F. The pellets may be composed at least in part of a material selected from the group of materials consisting of polystyrene, ABS plastic, nylon, neoprene, polyethylene, polypropylene and mixtures thereof.

In an important series of embodiments, the volume (200) may include a thermoactive binder (500) mixed with the plurality of pellets (400). Such a binder (500) may include a thermoactive adhesive having a viscosity of approximately 10,000 cps at a temperature of 250° Fahrenheit and a viscosity of approximately 2,000,000 cps at a temperature of 150° Fahrenheit. In other embodiments, the thermoactive binder may have a thermoactive adhesive having a viscosity at a temperature of 150° Fahrenheit that is at least ten times as great as a viscosity at 250° Fahrenheit.

In one particular embodiment, a moldable splint (10) may include a thermoplastic shell (100) having a shell material thickness (150), a first shell outside linear dimension (160), a second shell outside linear dimension (170) and a third shell outside linear dimension (180). These dimensions may enclose an at least partially fluid-filled volume (200) comprising a plurality of substantially hollow substantially spherical pellets (400) having at least one partially rounded edge and a thermoactive binder (500) having a viscosity at a temperature of 150° Fahrenheit that is at least ten times as great as a viscosity at 250° Fahrenheit mixed with the plurality of pellets (400). The volume (200) may be closed to an external atmosphere and bounded by a first shell inside linear dimension (165), a second shell inside linear dimension (175), and a third shell inside linear dimension (185), wherein the first shell outside linear dimension (160) is equal to or greater than the second shell outside linear dimension (170), and the third shell outside linear dimension (180) is less than or equal to the second shell outside linear dimension (170). The first shell inside linear dimension (165) may be greater than or equal to the second shell inside linear dimension (175), and the third shell inside linear dimension (185) may be less than or equal to the second shell inside linear dimension (175). The first shell outside linear dimension (160), the second shell outside linear dimension (170), the third shell outside linear dimension (180), the first shell inside linear dimension (165), the second shell inside linear dimension (175), and the third shell inside linear dimension (185) all may be equal to or greater than the shell material thickness (150).

In a further series from this embodiment, the thermoactive binder further may include a thermoactive adhesive having a viscosity of approximately 10,000 cps at a temperature of 250° Fahrenheit and/or a thermoactive adhesive having a viscosity of approximately 2,000,000 cps at a temperature of 150° Fahrenheit. In all embodiments, the volume (200) may include more than one thermoactive binder.

In one method of forming a moldable splint, consistent with the above description, the following steps may be followed: First, forming a hollow thermoplastic shell (100) enclosing an at least partially fluid filled volume (200). Then, filling the at least partially fluid filled volume with a slurry comprising a mixture of a thermoactive binder having a viscosity at a temperature of 150° Fahrenheit that is at least ten times as great as a viscosity at 250° Fahrenheit and a plurality of substantially hollow substantially spheroidal pellets.

The thermoplastic shell (100) may then be closed to an ambient atmosphere and cooled to an ambient atmosphere temperature. When ready for use, the shell may be heated to a first working temperature, which, in some embodiments, is 160°-180° Fahrenheit. The shell may then be molded to a body contour of a user, and cooled to the ambient atmosphere temperature.

Figure 10:
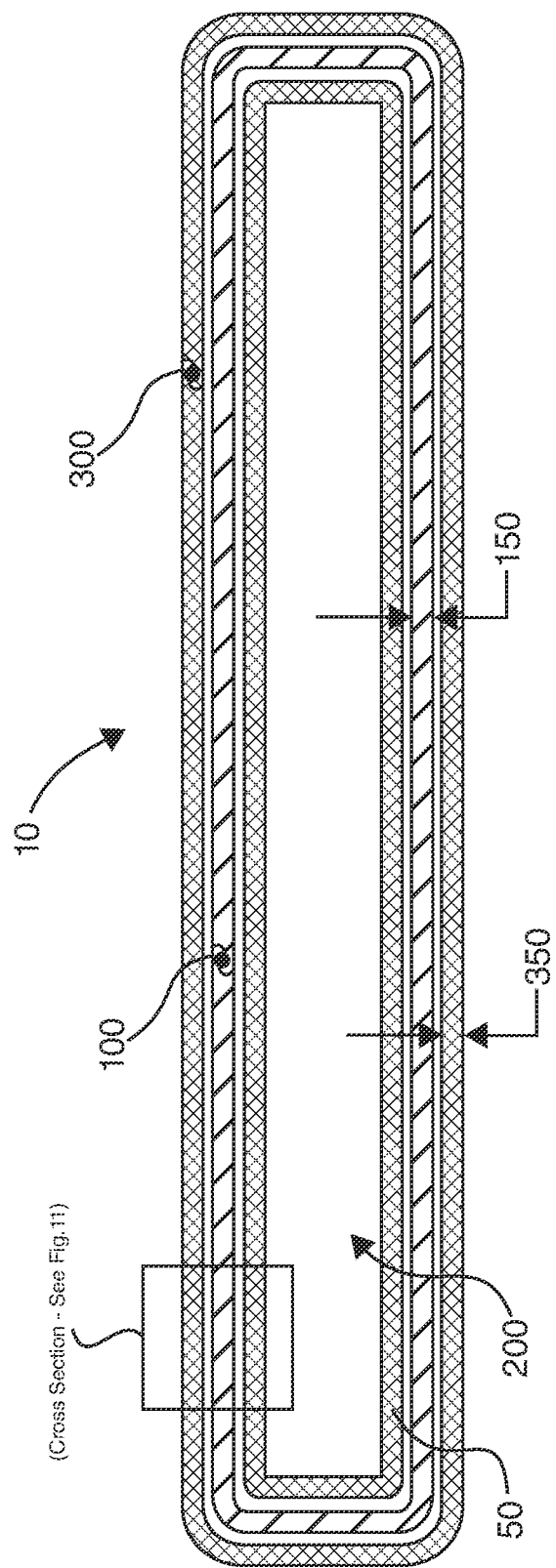
FIG. 10 is another embodiment of a moldable splint.
Figure 11:
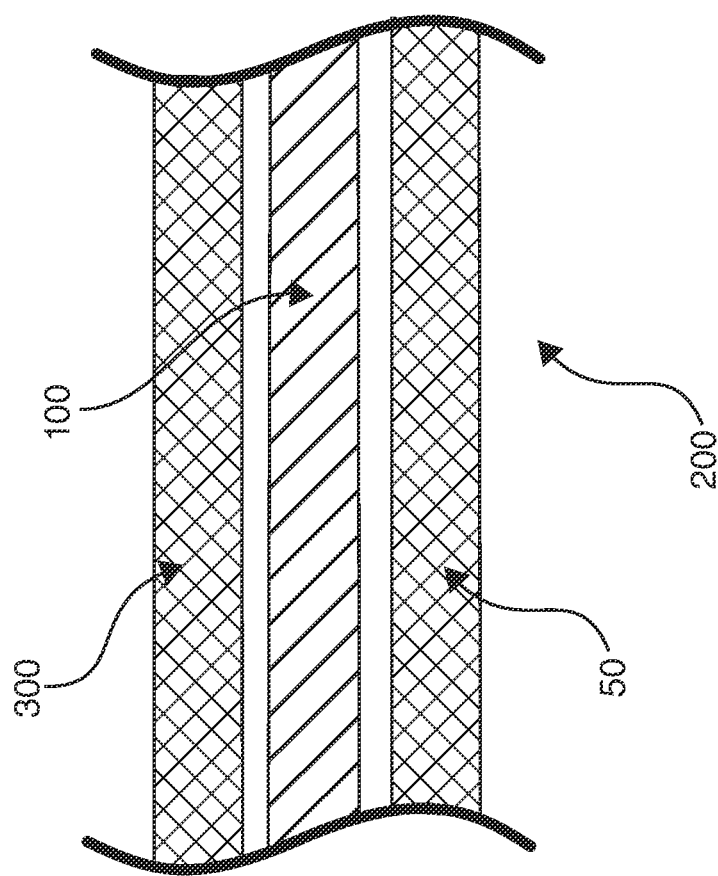
FIG. 11 is a cross-sectional view of a wall section of the embodiment of FIG. 10.

In another series of embodiments, seen well in FIGS. 10-14, a moldable splint (10) may include, as seen in FIGS. 10 and 11, a closed external cover (300), enclosing a moldable thermoplastic shell (100), closed to an external atmosphere. The shell (100) may have a shell material thickness (150), a first shell outside linear dimension (160), a second shell outside linear dimension (170) and a third shell outside linear dimension (180). The shell (100) may further enclose a closed internal liner (50), as seen again n FIGS. 10 and 11 that in turn encloses an at least partially fluid-filled at least biphasically reversibly fluid thermoplastic volume (200). The liner (50) may be externally bounded by a first shell inside linear dimension (165), a second shell inside linear dimension (175) and a third shell inside linear dimension (185), as seen in FIG. 4.

In other related embodiments, at least one of the cover (300) and the liner (50) may be of any type of flexible construction, which perforce includes woven construction, woven construction impregnated with a thermoplastic; and one or both of the cover (300) and the liner (50) may be laminated to the shell (100).

As seen across a wide range of embodiments, the thermoplastic shell (100) may be a thermoplastic having a melting temperature between about 140° F. (60° Celsius) and 212° F. (100° Celsius) and a crystallization temperature of about 140° F. (60° Celsius). Similarly, across a wide range of embodiments, the thermoplastic shell (100) further may include a thermoplastic selected from the group of thermoplastics consisting of poly (epsilon-caprolactone) (PCL), transpolyisoprene, transpolychloroprene and mixtures thereof. In a sub-series of embodiments, the thermoplastic shell (100) further may be cross-linked poly (epsilon-caprolactone) (PCL) having a shell material thickness (150) of between about 1.0 millimeters and 4.0 millimeters.

Figure 12:
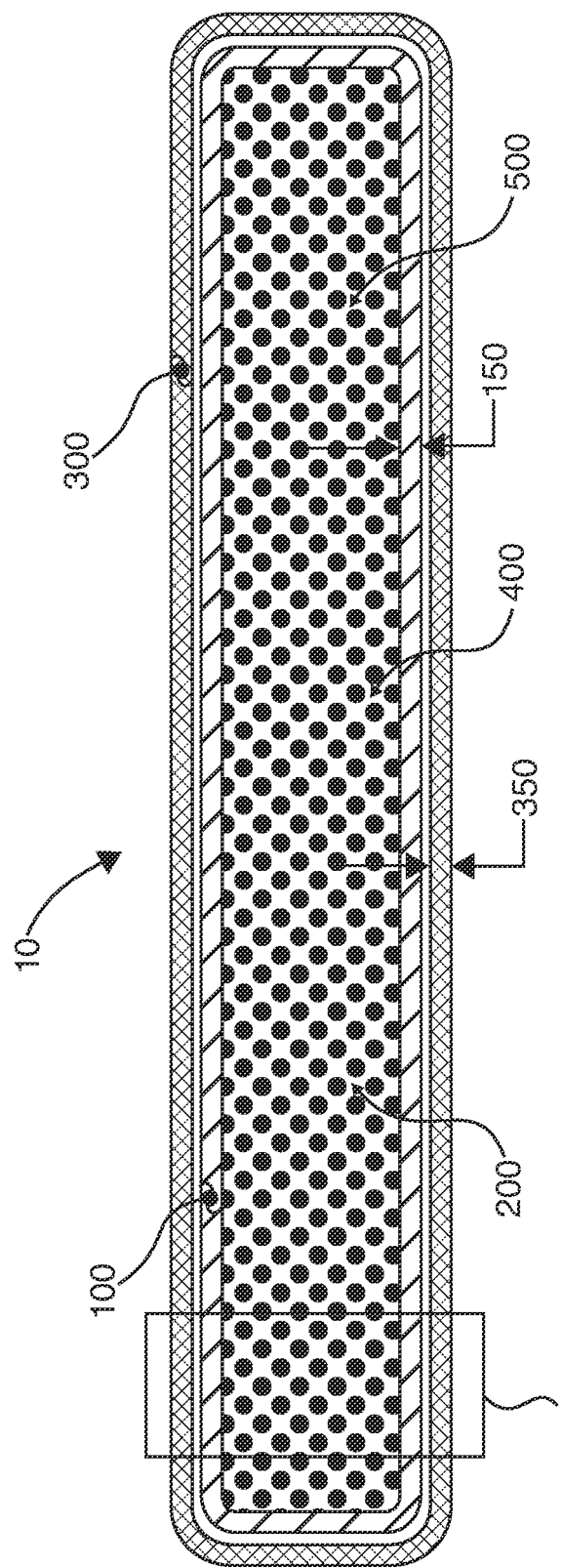
FIG. 12 is another embodiment of a moldable splint.
Figure 13:
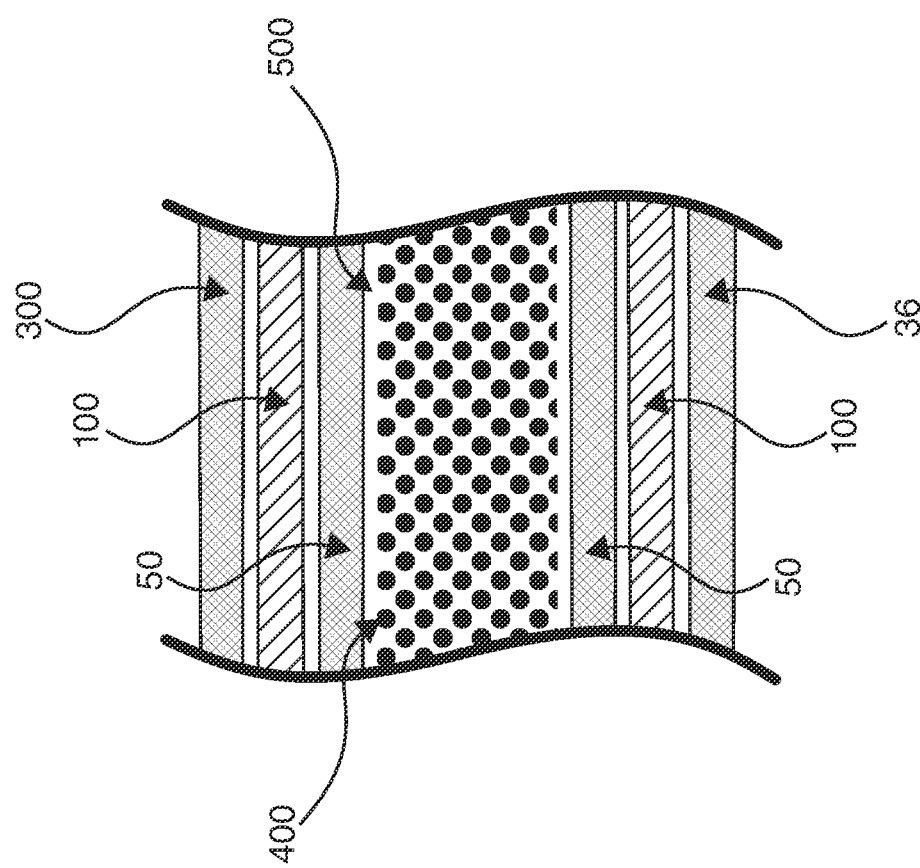
FIG. 13 is a cross-sectional view of a wall section of the embodiment of FIG. 12.

In some embodiments, seen well in FIGS. 12 and 13, the at least partially fluid filled volume (200) further may include a plurality of pellets (400) having at least one partially rounded edge. The pellets (400) may have a first substantially hollow substantially spheroidal shape having a diameter of approximately 1 millimeter to 6 millimeters at a temperature of about 70° F. (21° C.).

In other embodiments, the pellets (400) may have any one or more of: of a nominal density of about 1 lb. per cubic foot, a compressive strength (at 10% deformation) of approximately 10.0 pounds per square inch, a minimum flexural strength of approximately 25.0 pounds per square inch and may retain a second substantially spheroidal shape within 10% of the first substantially spheroidal shape when exposed to temperatures greater than 100° F. (38° C.) and less than 250° F. (93° C.). In some embodiments, the pellets (400) may at least partially be formed of at least one material selected from the group of materials consisting of polystyrene, ABS plastic, nylon, neoprene, polyethylene, polypropylene and mixtures thereof.

In yet another series of embodiments, seen well in FIGS. 2, 12 and 13, the volume (200) may further include a thermoactive binder (500) mixed with the plurality of pellets (400). The thermoactive binder may have, at least in part, a thermoactive adhesive having a viscosity of approximately 10,000 cps at a temperature of 250° Fahrenheit. Such thermoactive binders may further have a thermoactive adhesive having a viscosity of approximately 2,000,000 cps at a temperature of 150° Fahrenheit, and/or a thermoactive adhesive having a viscosity at a temperature of 150° Fahrenheit that is at least ten times as great as a viscosity at 250° Fahrenheit, as shown by way of example and not limitation in FIG. 9.

In one selected embodiment, by way of example only and not limitation, a moldable splint (10) may have a closed external cover (300) of woven construction that encloses a thermoplastic shell (100) having a shell material thickness (150), a first shell outside linear dimension (160), a second shell outside linear dimension (170) and a third shell outside linear dimension (180). The shell (100) may in turn enclose an at least partially fluid-filled volume (200), closed to an external atmosphere, bounded by a first shell inside linear dimension (165), a second shell inside linear dimension (175), and a third shell inside linear dimension (185). The first shell outside linear dimension (160) may be equal to or greater than the second shell outside linear dimension (170), and the third shell outside linear dimension (180) may be less than or equal to the second shell outside linear dimension (170), and the first shell inside linear dimension (165) may be greater than or equal to the second shell inside linear dimension (175), and the third shell inside linear dimension (185) may be less than or equal to the second shell inside linear dimension (175). The first shell outside linear dimension (160), the second shell outside linear dimension (170), the third shell outside linear dimension (180), the first shell inside linear dimension (165), the second shell inside linear dimension (175), and the third shell inside linear dimension (185) may all be equal to or greater than the shell material thickness (150)

Such a splint (10) may have a closed internal liner (50), seen well in FIGS. 12 and 13 of woven construction that encloses a plurality of substantially hollow substantially spherical pellets (400) having at least one partially rounded edge and a first substantially hollow substantially spheroidal shape having a diameter of approximately 1 millimeter to 6 millimeters at a temperature of about 70° F. (21° C.). The plurality of the pellets (400) will retain a second substantially spheroidal shape within 10% of the first substantially spheroidal shape when exposed to temperatures greater than 100° F. (38° C.) and less than 250° F. (93° C.). The pellets (400) may be mixed with a thermoactive binder (500) having a viscosity at a temperature of 150° Fahrenheit that is at least ten times as great as a viscosity at 250° Fahrenheit.

One skilled in the art will understand a variety of methods of forming the splint (10) as described above, one of which, by way of example and not limitation, is now described. Steps may include forming a liner (50) having at least one wall forming a liner length, liner width, and a liner thickness, a first closed liner end and a second open liner end, forming a partially closed liner volume having one open end, as seen well in FIG. 14, and designated therein as "OE".

Figure 14:
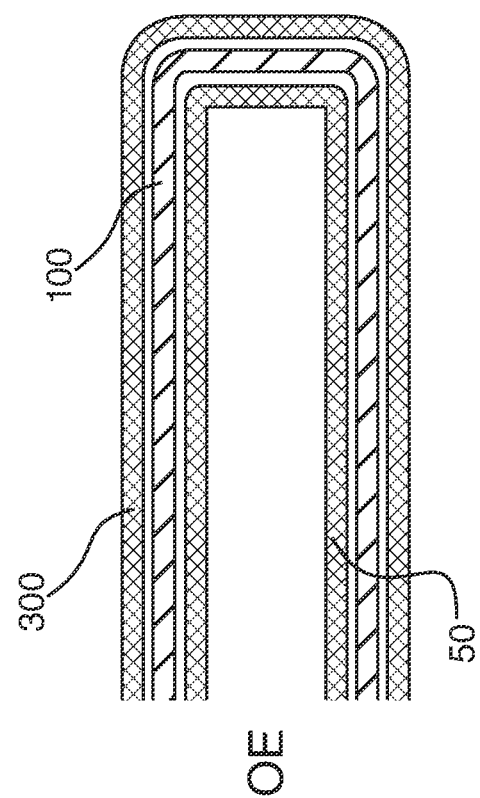
FIG. 14 illustrates an intermediate step in the method of forming the embodiment of FIGS. 10 and 12, wherein the liner, shell and cover are all shown assembled but open to allow filling with volume, and subsequent closure.

Such a liner (50) may be placed within a moldable hollow thermoplastic shell (100) having at least one shell wall having a shell material thickness (150) and forming a shell length, shell width, and shell thickness, a first closed shell end and a second open shell end, forming a partially closed shell volume having one open end, such that the liner closed end is adjacent the shell closed end, and the liner open end is adjacent the shell open end, again as seen well in FIG. 14.

Subsequently, the partially closed liner (500), shell (100), and cover (300) may be fully closed to create a closed at least partially fluid-filled at least biphasically reversible thermoplastic volume (200) contained within the splint (10), in the following manner: closing the liner (50) to fully contain the fluid-filled at least biphasically reversible thermoplastic volume (200), closing the moldable hollow thermoplastic shell (100) to contain the woven liner (50) containing the fluid-filled at least biphasically reversible thermoplastic volume (200), and finally, enclosing the moldable hollow thermoplastic shell (100) in an external cover (300), having at least one wall forming a cover length, width and thickness, a first closed cover end and a second open cover end. Then the closing of the external cover (300) to contain the moldable thermoplastic shell (100), enclosing the liner (50), enclosing the at least partially fluid-filled at least biphasically reversible thermoplastic volume (200) completes the process.

In some embodiments, the step of closing at least one of the internal liner (50), the external cover (300), and the moldable hollow thermoplastic shell (200), consists of closure by a method selected from sewing, thermal closure, chemical closure, welding and mechanical closure with a mechanical closing device.

Those embodiments utilizing an inner liner (50) have been shown to have many advantages. When the thermoplastic shell (100) is heated, it becomes quite tacky and self-adherent. During the filling of the partially fluid filled volume (200), with or without pellets (400), opposing sides of the thermoplastic shell may adhere to one another, deforming the splint and making it difficult or impossible to use. Similarly, since the splint according to the present invention(s) can be reheated and re-formed, the liner (50) prevents self-adherence of the sides of the shell (100) during such manipulation. Likewise, the external cover (300) confers many advantages, including patient or user comfort and prevention of self-adherence of the shell (100) when the splint (10) is bent. The external cover (300) also minimizes the tendency of the splint (10) to stick to packaging, surfaces, or other splints (10), for example, while in storage.

Numerous alterations, modifications, and variations of the preferred embodiments disclosed herein will be apparent to those skilled in the art and they are all anticipated and contemplated to be within the spirit and scope of the disclosed specification. For example, although specific embodiments have been described in detail, those with skill in the art will understand that the preceding embodiments and variations can be modified to incorporate various types of substitute and or additional or alternative materials, relative arrangement of elements, order of steps and additional steps, and dimensional configurations. Accordingly, even though only few variations of the method and products are described herein, it is to be understood that the practice of such additional modifications and variations and the equivalents thereof, are within the spirit and scope of the method and products as defined in the following claims. The corresponding structures, materials, acts, and equivalents of all means or step plus function elements in the claims below are intended to include any structure, material, or acts for performing the functions in combination with other claimed elements as specifically claimed.

I claim:

1. A moldable splint (10) comprising:
  a closed external cover (300), enclosing,
  a moldable thermoplastic shell (100), closed to an external atmosphere, having a shell material thickness (150), a first shell outside linear dimension (160), a second shell outside linear dimension (170) and a third shell outside linear dimension (180) enclosing,
  a closed internal liner (50), enclosing,
  an at least partially fluid-filled at least biphasically reversibly fluid thermoplastic volume (200), and the liner (50) is externally bounded by a first shell inside linear dimension (165), a second shell inside linear dimension (175) and a third shell inside linear dimension (185).

2. The moldable splint according to claim 1, wherein at least one of the cover (300) and the liner (50) is of woven construction.

3. The moldable splint according to claim 1, wherein at least one of the cover (300) and the liner (50) is of woven construction impregnated with a thermoplastic.

4. The moldable splint (10) according to claim 1, wherein at least one of the cover (300) and the liner (50) is laminated to the shell (100).

5. The splint (10) according to claim 1, wherein the thermoplastic shell (100) comprises a thermoplastic having a melting temperature between about 140° F. (60° Celsius) and 212° F. (100° Celsius) and a crystallization temperature of about 140° F. (60° Celsius).

6. The splint (10) according to claim 1, wherein the thermoplastic shell (100) further comprises a thermoplastic selected from the group of thermoplastics consisting of poly (epsilon-caprolactone) (PCL), transpolyisoprene, transpolychloroprene and mixtures thereof.

7. The splint (10) according to claim 1, wherein the thermoplastic shell (100) further comprises cross-linked poly (epsilon-caprolactone) (PCL) having a shell material thickness (150) of between about 1.0 millimeters and 4.0 millimeters.

8. The splint (10) according to claim 1, wherein the at least partially fluid filled volume (200) further comprises a plurality of pellets (400) having at least one partially rounded edge.

9. The splint (10) according to claim 8, wherein a plurality of the pellets (400) has a first substantially hollow substantially spheroidal shape having a diameter of approximately 1 millimeter to 6 millimeters at a temperature of about 70° F. (21° C.).

10. The splint (10) according to claim 9, wherein a plurality of the pellets (400) will retain a second substantially spheroidal shape within 10% of the first substantially spheroidal shape when exposed to temperatures greater than 100° F. (38° C.) and less than 250° F. (93° C.).

11. The splint (10) according to claim 8, wherein a plurality of the pellets (400) has a nominal density of about 1 lb. per cubic foot.

12. The splint (10) according to claim 8, wherein a plurality of the pellets (400) has a compressive strength (at 10% deformation) of approximately 10.0 pounds per square inch.

13. The splint (10) according to claim 8, wherein a plurality of the pellets (400) has a minimum flexural strength of approximately 25.0 pounds per square inch.

14. The splint (10) according to claim 8, wherein a plurality of the pellets (400) further comprises at least one material selected from the group of materials consisting of polystyrene, ABS plastic, nylon, neoprene, polyethylene, polypropylene and mixtures thereof.

15. The splint (10) according to claim 8, wherein the volume (200) further comprises a thermoactive binder (500) mixed with the plurality of pellets (400).

16. The splint according to claim 15, wherein the thermoactive binder further comprises a thermoactive adhesive having a viscosity of approximately 10,000 cps at a temperature of 250° Fahrenheit.

17. The splint according to claim 15, wherein the thermoactive binder further comprises a thermoactive adhesive having a viscosity of approximately 2,000,000 cps at a temperature of 150° Fahrenheit.

18. The splint according to claim 15, wherein the thermoactive binder further comprises a thermoactive adhesive having a viscosity at a temperature of 150° Fahrenheit that is at least ten times as great as a viscosity at 250° Fahrenheit.

19. A moldable splint (10) comprising:
  a closed external cover (300) of woven construction, enclosing,
  a thermoplastic shell (100) having a shell material thickness (150), a first shell outside linear dimension (160), a second shell outside linear dimension (170) and a third shell outside linear dimension (180) enclosing an at least partially fluid-filled volume (200), closed to an external atmosphere, bounded by a first shell inside linear dimension (165), a second shell inside linear dimension (175), and a third shell inside linear dimension (185), wherein the first shell outside linear dimension (160) is equal to or greater than the second shell outside linear dimension (170), and the third shell outside linear dimension (180) is less than or equal to the second shell outside linear dimension (170), and wherein the first shell inside linear dimension (165) is greater than or equal to the second shell inside linear dimension (175), and the third shell inside linear dimension (185) is less than or equal to the second shell inside linear dimension (175), and wherein the first shell outside linear dimension (160), the second shell outside linear dimension (170), the third shell outside linear dimension (180), the first shell inside linear dimension (165), the second shell inside linear dimension (175), and the third shell inside linear dimension (185) are all equal to or greater than the shell material thickness (150), enclosing, a closed internal liner (50) of woven construction, enclosing, a plurality of substantially hollow substantially spherical pellets (400) having at least one partially rounded edge and a first substantially hollow substantially spheroidal shape having a diameter of approximately 1 millimeter to 6 millimeters at a temperature of about 70° F. (21° C.), and the plurality of the pellets (400) will retain a second substantially spheroidal shape within 10% of the first substantially spheroidal shape when exposed to temperatures greater than 100° F. (38° C.) and less than 250° F. (93° C.), and a thermoactive binder (500) having a viscosity at a temperature of 150° Fahrenheit that is at least ten times as great as a viscosity at 250° Fahrenheit mixed with the plurality of pellets (400).

20. A method of forming a moldable splint (10), comprising the steps of:

a. forming a liner (50) having at least one wall forming a liner length, liner width, and a liner thickness, a first closed liner end and a second open liner end, forming a partially closed liner volume having one open end, b. placing the liner (50) within a moldable hollow thermoplastic shell (100) having at least one shell wall having a shell material thickness (150) forming a shell length, shell width, and shell thickness, a first closed shell end and a second open shell end, forming a partially closed shell volume having one open end, such that the liner closed end is adjacent the shell closed end, and the liner open end is adjacent the shell open end, c. filling the partially closed shell volume to create an at least partially fluid-filled at least biphasically reversible thermoplastic volume (200), d. closing the liner (50) to fully contain the fluid-filled at least biphasically reversible thermoplastic volume (200), e. closing the moldable hollow thermoplastic shell (100) to contain the woven liner (50) containing the fluid-filled at least biphasically reversible thermoplastic volume (200), and f. enclosing the moldable hollow thermoplastic shell (100) in an external cover (300), having at least one wall forming a cover length, width and thickness, a first closed cover end and a second open cover end, and g. closing the external cover (300) to contain the moldable thermoplastic shell (100), enclosing the liner (50), enclosing the at least partially fluid-filled at least biphasically reversible thermoplastic volume (200).

21. The method according to claim 20, wherein the step of closing at least one of the liner (50), the external cover (300), and the moldable hollow thermoplastic shell (200), consists of closure by a method selected from sewing, thermal closure, chemical closure, welding and mechanical closure with a mechanical closing device.

* * * * *